(12) United States Patent
Imamura et al.

(10) Patent No.: US 8,969,807 B2
(45) Date of Patent: Mar. 3, 2015

(54) CARRIER AND ADHESION AMOUNT MEASURING APPARATUS, AND MEASURING METHOD, PROGRAM, AND RECORDING MEDIUM OF THE SAME

(71) Applicants: Motoki Imamura, Miyagi (JP); Shigeki Nishina, Miyagi (JP)

(72) Inventors: Motoki Imamura, Miyagi (JP); Shigeki Nishina, Miyagi (JP)

(73) Assignee: Advantest Corporation, Tokyo (JP)

( * ) Notice: Subject to any disclaimer, the term of this patent is extended or adjusted under 35 U.S.C. 154(b) by 19 days.

(21) Appl. No.: 13/679,081

(22) Filed: Nov. 16, 2012

(65) Prior Publication Data

US 2013/0075612 A1 Mar. 28, 2013

Related U.S. Application Data

(62) Division of application No. 12/608,208, filed on Oct. 29, 2009, now abandoned.

(30) Foreign Application Priority Data

Oct. 28, 2009 (JP) .................. 2009-247872

(51) Int. Cl.
  *G01J 5/02* (2006.01)
  *G01N 21/17* (2006.01)
  *G01N 21/3581* (2014.01)
  *G01N 21/3504* (2014.01)
(52) U.S. Cl.
  CPC ............ *G01N 21/17* (2013.01); *G01N 21/3581* (2013.01); *G01N 21/3504* (2013.01)
  USPC .................... 250/341.1; 250/336.1
(58) Field of Classification Search
  USPC ........................... 250/341.1, 336.1
  See application file for complete search history.

(56) References Cited

U.S. PATENT DOCUMENTS

| | | | |
|---|---|---|---|
| 5,863,508 A | 1/1999 | Lachman et al. | |
| 8,319,183 B2 * | 11/2012 | Gunasekaran et al. | .... 250/341.5 |
| 2010/0235114 A1 * | 9/2010 | Levy et al. | ...................... 702/40 |

FOREIGN PATENT DOCUMENTS

| | | |
|---|---|---|
| JP | 64-1930 | 1/1989 |
| JP | 5-131118 | 5/1993 |
| JP | 11-107744 | 4/1999 |
| JP | 2009-57948 | 3/2009 |
| WO | 2009/031600 | 3/2009 |

OTHER PUBLICATIONS

Japan Office action, dated May 23, 2013 along with an english translation thereof.

* cited by examiner

*Primary Examiner* — Christine Sung
(74) *Attorney, Agent, or Firm* — Greenblum & Bernstein, P.L.C.

(57) ABSTRACT

A carrier includes attachment holes to which a catalyst attaches, and non-attachment holes to which the catalyst does not attach. An attachment quantity measurement device includes an electromagnetic wave output device that outputs a terahertz wave toward the carrier, an electromagnetic wave detector that detects the terahertz wave which has transmitted through the carrier, a reference value obtainer that obtains, based on a result detected by the electromagnetic wave detector, any one of an absorption rate, a group delay, and a dispersion of the terahertz wave in the non-attachment holes, and an attachment quantity obtainer that obtains, based on the result detected by the electromagnetic wave detector and the result obtained by the reference value obtainer, a weight or a density of the catalyst present in the attachment holes.

18 Claims, 7 Drawing Sheets

CARRIER AND ADHESION AMOUNT MEASURING APPARATUS, AND MEASURING METHOD, PROGRAM, AND RECORDING MEDIUM OF THE SAME

CROSS-REFERENCE RELATED TO RELATED APPLICATION

This application is a divisional of pending U.S. patent application Ser. No. 12/608,208, filed Oct. 29, 2009, which claims priority to Japanese Application No. 2009-247872, filed Oct. 28, 2009, which are expressly incorporated herein by their entireties.

BACKGROUND ART

1. Field of the Invention

The present invention relates to measurement of a density of a catalyst or promoter component in a carrier to which the catalyst or promoter is attached using an electromagnetic wave (frequency thereof is equal to or more than 0.01 [THz], and equal to or less than 100 [THz]) (such as a terahertz wave (frequency thereof is equal to or more than 0.03 [THz], and equal to or less than 10 [THz]), for example).

2. Description of the Prior Art

Conventionally, a carrier made of a ceramic has been immersed in a solution or suspension of a catalyst or promoter, the catalyst or promoter attaches to the carrier, and an oxidation catalyst for automobiles and the like and an electrode for a fuel cell are then obtained.

It should be noted that the applicant does not know prior art documents describing the measurement of the quantity of the catalyst or promoter (such as density) attached to the carrier.

SUMMARY OF THE INVENTION

It is an object of the present invention to measure a quantity of attachment (such as density) of a material (such as catalyst and promoter) attached to a carrier.

According to the present invention, a carrier includes: an attachment hole to which a predetermined component attaches; and a non-attachment hole to which the predetermined component does not attach.

According to the thus constructed carrier, a predetermined component attaches to an attachment hole. The predetermined component does not attach to a non-attachment hole.

According to the carrier of the present invention, the direction of an extension of the attachment hole and the direction of an extension of the non-attachment hole may be parallel with each other.

The carrier according to the present invention may includes two end surfaces that are parallel with each other, wherein the attachment hole and the non-attachment hole open on the two end surfaces.

The present invention is a method of manufacturing the carrier of the present invention, wherein the carrier includes a plurality of holes having a first opening portion and a second opening portion on an opposite side with respect to the first opening portion, the method of manufacturing the carrier including: a step of closing the first opening portion and the second opening portion of a part of the plurality of holes; and a step of immersing the carrier in a liquid in which the predetermined component is present.

The present invention is a method of manufacturing the carrier of the present invention, wherein the carrier includes a plurality of holes having a first opening portion and a second opening portion on an opposite side with respect to the first opening portion, and a first end surface on which the first opening portion opens, the method of manufacturing the carrier including: a step of closing the first opening portion of a part of the plurality of holes; and a step of splaying, toward the first end surface, a liquid in which the predetermined component is present.

The present invention is a method of manufacturing the carrier of the present invention, wherein the carrier includes a plurality of holes having a first opening portion and a second opening portion on an opposite side with respect to the first opening portion, a first end surface on which the first opening portion opens, and a second end surface on which the second opening portion opens, the method of manufacturing the carrier including: a step of closing the second opening portion of a part of the plurality of holes; and a step of immersing the carrier in a liquid in which the predetermined component is present such that the liquid surface of the liquid is higher than the second end surface and lower than the first end surface.

The present invention is a method of manufacturing the carrier of the present invention, wherein the carrier includes a plurality of holes having a first opening portion and a second opening portion on an opposite side with respect to the first opening portion, and a first end surface on which the first opening portion opens, the method of manufacturing the carrier including: a step of immersing the carrier in a liquid in which the predetermined component is present such that the liquid surface of the liquid is lower than the first opening portion of a part of the plurality of holes.

According to the present invention, an attachment quantity measurement device includes: an electromagnetic wave output device that outputs an electromagnetic wave to be measured having a frequency equal to or higher than 0.01 [THz] and equal to or lower than 100 [THz] toward the carrier of the present invention; an electromagnetic wave detector that detects the electromagnetic wave to be measured which has transmitted through the carrier; a reference value deriving unit that derives, based on a result detected by the electromagnetic wave detector, any one of an absorption rate, a group delay, and a dispersion of the electromagnetic wave to be measured in the non-attachment hole; and an attachment quantity deriving unit that derives, based on the result detected by the electromagnetic wave detector and the result derived by the reference value deriving unit, a weight or a density of the predetermined component present in the attachment hole.

According to the thus constructed attachment quantity measurement device, an electromagnetic wave output device outputs an electromagnetic wave to be measured having a frequency equal to or higher than 0.01 [THz] and equal to or lower than 100 [THz] toward the carrier of the present invention. An electromagnetic wave detector detects the electromagnetic wave to be measured which has transmitted through the carrier. A reference value deriving unit derives, based on a result detected by the electromagnetic wave detector, any one of an absorption rate, a group delay, and a dispersion of the electromagnetic wave to be measured in the non-attachment hole. An attachment quantity deriving unit derives, based on the result detected by the electromagnetic wave detector and the result derived by the reference value deriving unit, a weight or a density of the predetermined component present in the attachment hole.

According to the present invention, the attachment quantity measurement device of the present invention, includes: a rotational drive unit that rotates the carrier or a travel direction of the electromagnetic wave to be measured while a line in a direction perpendicular to the travel direction of the electromagnetic wave to be measured is set as a rotational axis; and a linear drive unit that moves the carrier or the travel direction of the electromagnetic wave to be measured in a direction perpendicular to the travel direction of the electromagnetic wave to be measured and the rotational axis, wherein the detection is carried out by the electromagnetic wave detector while the rotational drive unit and the linear drive unit are operating.

The present invention is an attachment quantity measurement method using an attachment quantity measurement device including: an electromagnetic wave output device that outputs an electromagnetic wave to be measured having a frequency equal to or higher than 0.01 [THz] and equal to or lower than 100 [THz] toward the carrier of the present invention; and an electromagnetic wave detector that detects the electromagnetic wave to be measured which has transmitted through the carrier; the attachment quantity measurement method including: a reference value deriving step that derives, based on a result detected by the electromagnetic wave detector, any one of an absorption rate, a group delay, and a dispersion of the electromagnetic wave to be measured in the non-attachment hole; and an attachment quantity deriving step that derives, based on the result detected by the electromagnetic wave detector and the result derived by the reference value deriving step, a weight or a density of the predetermined component present in the attachment hole.

The present invention is a program of instructions for execution by a computer to perform an attachment quantity measurement process using an attachment quantity measurement device including: an electromagnetic wave output device that outputs an electromagnetic wave to be measured having a frequency equal to or higher than 0.01 [THz] and equal to or lower than 100 [THz] toward the carrier of the present invention; and an electromagnetic wave detector that detects the electromagnetic wave to be measured which has transmitted through the carrier; the attachment quantity measurement process including: a reference value deriving step that derives, based on a result detected by the electromagnetic wave detector, any one of an absorption rate, a group delay, and a dispersion of the electromagnetic wave to be measured in the non-attachment hole; and an attachment quantity deriving step that derives, based on the result detected by the electromagnetic wave detector and the result derived by the reference value deriving step, a weight or a density of the predetermined component present in the attachment hole.

The present invention is a computer-readable medium having a program of instructions for execution by a computer to perform an attachment quantity measurement process using an attachment quantity measurement device including: an electromagnetic wave output device that outputs an electromagnetic wave to be measured having a frequency equal to or higher than 0.01 [THz] and equal to or lower than 100 [THz] toward the carrier of the present invention; and an electromagnetic wave detector that detects the electromagnetic wave to be measured which has transmitted through the carrier; the attachment quantity measurement process including: a reference value deriving step that derives, based on a result detected by the electromagnetic wave detector, any one of an absorption rate, a group delay, and a dispersion of the electromagnetic wave to be measured in the non-attachment hole; and an attachment quantity deriving step that derives, based on the result detected by the electromagnetic wave detector and the result derived by the reference value deriving step, a weight or a density of the predetermined component present in the attachment hole.

BRIEF DESCRIPTION OF THE DRAWINGS

FIGS. 2(a) and 2(b) show a configuration of an attachment quantity measurement device according to the first embodiment, in which FIG. 2(a) is a plan view and FIG. 2(b) is a partial front view;

FIGS. 6(a) and 6(b) are partial cross-sectional views of the carrier 1 according to the fourth embodiment, in which FIG. 6(a) is a partial cross-sectional view of the carrier 1 when the carrier 1 is being immersed in the solution 110 (corresponding to FIG. 3(b)), and FIG. 6(b) is a partial cross-sectional view of the carrier 1 after the immersion in the solution 110 (corresponding to FIG. 3(b))

BEST MODE FOR CARRYING OUT THE INVENTION

Figure 1:
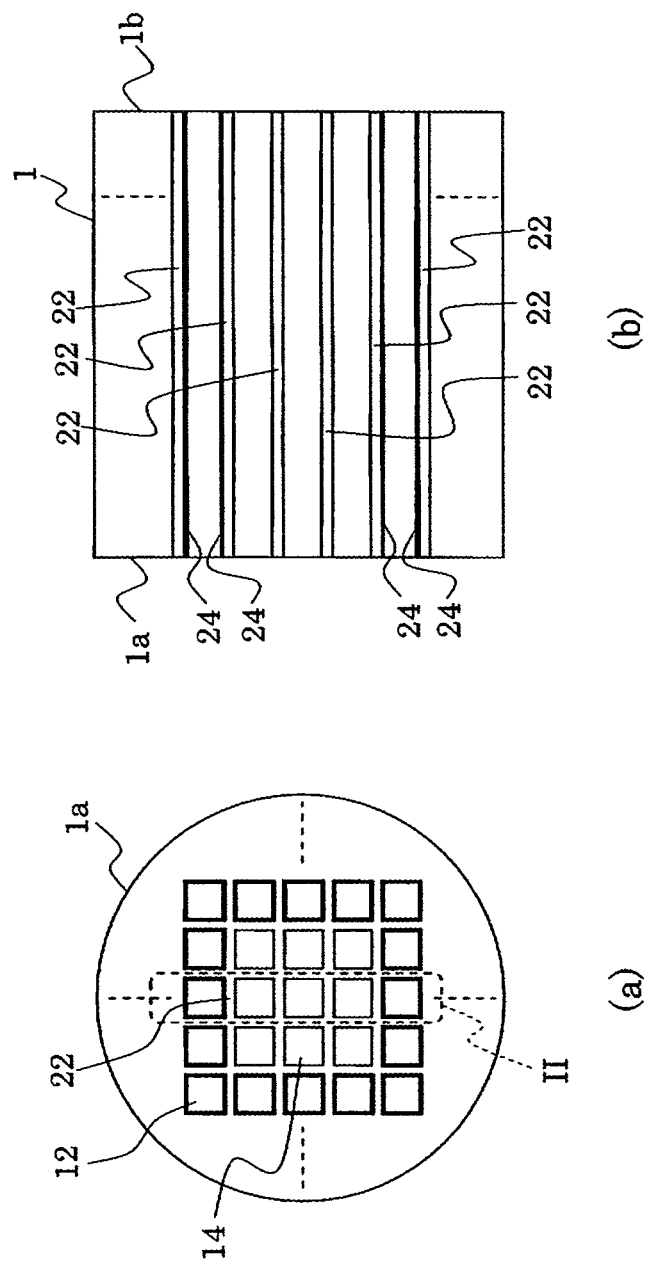
FIG. 1(a) is a front view of a carrier 1 according to a first embodiment of the present invention.
FIG. 1(b) is a cross-sectional view of a part II of the carrier 1.

A description will now be given of embodiments of the present invention with reference to drawings.

First Embodiment

FIG. 1(a) is a front view of a carrier 1 according to a first embodiment of the present invention, and FIG. 1(b) is a cross-sectional view of a part II of the carrier 1.

The carrier 1 according to the first embodiment includes a first end surface 1a, and a second end surface 1b (refer to FIG. 1(b)). The first end surface 1a and second end surface 1b are parallel with each other. The first end surface 1a and second end surface 1b are circular (refer to FIG. 1(a)), and the carrier 1 itself is cylindrical. The carrier 1 is made of a ceramic.

The carrier 1 according to the first embodiment includes attachment holes 12 and non-attachment holes 14. In FIG. 1(a), the attachment holes 12 and non-attachment holes 14 are shown only in a vicinity of the center (the same applies to FIGS. 3(a), 3(b), and 7).

It should be noted that the non-attachment holes 14 are arranged approximately at the center of the first end surface 1a in FIG. 1(a). However, the non-attachment holes 14 may not be arranged approximately at the center of the first end surface 1a, and may be arranged in a portion close to the periphery of the first end surface 1a.

The attachment holes 12 and the non-attachment holes 14 are separated from each other by partition walls 22.

A predetermined component is attached to the attachment holes 12 (inner surfaces of the partition walls 22 enclosing the attachment holes 12). The attached predetermined component is a catalyst 24, for example. The predetermined component is not attached to the non-attachment holes 14. The catalyst (predetermined component) 24 attached to the attachment holes 12 serves as a catalyst which purifies an exhaust gas passing through the attachment holes 12. The catalyst (predetermined component) 24 is not attached to the non-attachment holes 14, and actions such as the purification of the exhaust gas and the like is not expected in the non-attachment holes 14.

It should be noted that the attachment hole 12 and the non-attachment hole 14 are distinguished from each other according to presence/absence of the attachment of the catalyst 24 in FIG. 1. On this occasion, the number of the types of the catalyst and promoter attached to the carrier 1 is not limited to one, and multiple types of them may be attached. For example, while catalysts A, B, and C are attached to the attachment holes 12, only the catalysts A and B are attached to the non-attachment holes 14, but the catalyst C is not.

The direction of the extension of the attachment holes 12 and that of the non-attachment holes 14 are parallel with each other, and both of them are perpendicular to the first end surface 1a and the second end surface 1b.

The attachment holes 12 and the non-attachment holes 14 open on the first end surface 1a as well as on the second end surface 1b. In other words, the attachment holes 12 and the non-attachment holes 14 pass through the carrier 1.

It is assumed that the number of the non-attachment holes 14 is extremely lower than that of the attachment holes 12. As a result, a decrease in performance (such as the purification of the exhaust gas) of the carrier 1 due to the presence of the non-attachment holes 14 is negligible.

A description will now be given of a usage of the carrier 1 according to the first embodiment.

An exhaust gas or the like flows from the first end surface 1a into the attachment holes 12. Then, the catalyst 24 attached to the attachment holes 12 (surfaces on the side of the attachment holes 12 of the partition walls 22 enclosing the attachment holes 12) causes a chemical reaction, and the exhaust gas passes through the attachment holes 12 while being purified, and is exhausted from the second end surface 1b.

It should be noted that, before (or after) the carrier 1 is used as described above, the quantity of the catalyst 24 attached to the carrier 1 is measured.

Figure 2:
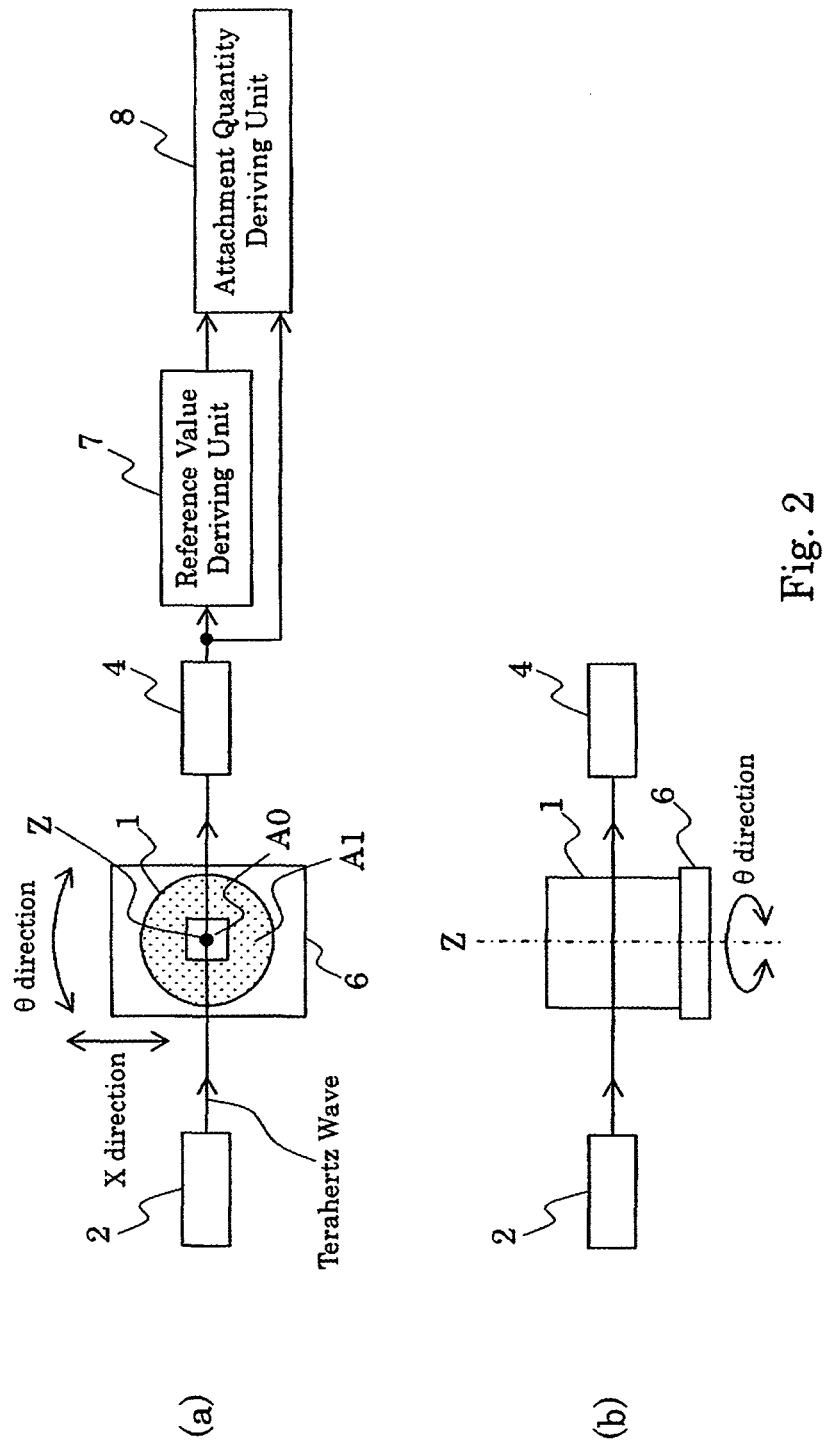

FIGS. 2(a) and 2(b) show a configuration of an attachment quantity measurement device according to the first embodiment, in which FIG. 2(a) is a plan view and FIG. 2(b) is a partial front view. The attachment quantity measurement device according to the first embodiment includes an electromagnetic wave output device 2, an electromagnetic wave detector 4, a scanning stage (rotational drive unit and a linear drive unit) 6, a reference value deriving unit 7, and an attachment quantity deriving unit 8.

In FIG. 2(a), a portion of the non-attachment holes 14 of the carrier 1 (referring to FIG. 1(a), three by three of non-attachment holes 14 at the center) is designated as a reference area A0, and an area other than the reference area A0 is designated as a collection area A1. It should be noted that the carrier 1, the electromagnetic wave output device 2, the electromagnetic wave detector 4, and the scanning stage 6 are shown, and the reference value deriving unit 7 and the attachment quantity deriving unit 8 are omitted in FIG. 2(b).

The electromagnetic wave output device 2 outputs an electromagnetic wave at a frequency equal to or more than 0.01 [THz] and equal to or less than 100 [THz] (referred to as "electromagnetic wave to be measured" hereinafter) toward the carrier 1. The frequency of the electromagnetic wave to be measured output toward the carrier 1 includes a terahertz wave band (such as equal to or more than 0.03 [THz] and equal to or less than 10 [THz]). According to the embodiment of the present invention, it is assumed that a terahertz wave is employed as an example of the electromagnetic wave to be measured.

The terahertz wave output to the carrier 1 transmits through the carrier 1. The electromagnetic wave detector 4 detects the electromagnetic wave to be measured (such as a terahertz wave) which has transmitted through the carrier 1.

The scanning stage (rotational drive unit and linear drive unit) 6 rotates the carrier 1 while a line Z orthogonal to the travel direction of the electromagnetic wave to be measured is set as a rotational axis (rotation in a θ direction). It should be noted that the electromagnetic wave output device 2 and the electromagnetic wave detector 4 may be rotated while the line Z is set as a rotational axis (which corresponds to the rotation of the travel direction of the electromagnetic wave to be measured).

The scanning stage 6 moves the carrier 1 in a direction X orthogonal to the travel direction of the electromagnetic wave to be measured and to the rotational axis Z (movement in the X direction). It should be noted that the electromagnetic wave output device 2 and the electromagnetic wave detector 4 may be moved in the X direction (which corresponds to the movement of the travel direction of the electromagnetic wave to be measured).

While the scanning stage (rotational drive unit and linear drive unit) 6 is in operation, the detection by the electromagnetic wave detector 4 is carried out.

The reference value deriving unit 7 derives, based on a result detected by the electromagnetic wave detector 4, any one of an absorption rate, a group delay, and a dispersion of the terahertz wave in the non-attachment holes 14. The absorption rate and the like of the terahertz wave in the non-attachment holes 14 can be derived by the widely-known computer tomography (CT).

The attachment quantity deriving unit 8 derives, based on the result detected by the electromagnetic wave detector 4 and the result derived by the reference value deriving unit 7, a weight (unit thereof is [g], for example) or a density (unit thereof [g/l] (weight per liter), for example) of the catalyst 24 present in the attachment holes 12.

A description will now be given of an example for causing the attachment quantity deriving unit 8 to derive, based on the absorption rate of the terahertz wave in the non-attachment holes 14, the density of the catalyst 24 present in the attachment holes 12.

The absorption rate of the terahertz wave when the density of the catalyst 24 is 0 is denoted by $\alpha 0$, an increase rate of the absorption rate of the terahertz wave with respect to the density of the catalyst 24 is denoted by $\beta$, and the absorption rate of the terahertz wave in the attachment holes 12 is denoted by $\alpha$. Then, the density of the catalyst 24 is represented as $(\alpha - \alpha 0)/\beta$. It should be noted that 13 is obtained in advance, and is recorded in the attachment quantity deriving unit 8.

Since the catalyst 24 is not attached to the non-attachment holes 14, it is considered that the density of the catalyst 24 is 0. Thus, the absorption rate of the terahertz wave in the non-attachment holes 14 derived by the reference value deriving unit 7 is considered as $\alpha 0$. Thus, the attachment quantity deriving unit 8 can acquire $\alpha 0$ from the reference value deriving unit 7.

Moreover, the attachment quantity deriving unit 8 derives a distribution of the absorption rate $\alpha$ of the terahertz wave in the attachment holes 12 from the result detected by the electromagnetic wave detector 4 by the widely-known CT.

Further, the attachment quantity deriving unit 8 assigns $\beta$, $\alpha 0$, and $\alpha$ to $(\alpha - \alpha 0)/\beta$, thereby deriving a distribution of the density of the catalyst 24 present in the attachment holes 12.

As described before, while the catalysts A, B, and C are attached to the attachment holes 12, it is conceivable that only the catalysts A and B are attached to the non-attachment holes 14, but the catalyst C is not. In this case, a distribution of the density of the catalyst C present in the attachment holes 12 is to be derived.

It should be noted that the reference value deriving unit 7 and the attachment quantity deriving unit 8 may be realize in the following manner. A computer is provided with a CPU, a hard disk, and a media (such as a floppy disk (registered trademark) and a CD-ROM) reader, and the media reader is caused to read a medium recording a program realizing the reference value deriving unit 7 and the attachment quantity deriving unit 8, thereby installing the program on the hard disk. This method may also realize the above-described functions.

According to the first embodiment, since the non-attachment holes 14 exist inside the carrier 1 to be measured, an error caused by a passage of time and an error caused by an individual difference of the carrier 1 can be neglected. Thus, the characteristics (such as the absorption rate) of the terahertz wave can be precisely measured when the density of the catalyst 24 is zero in the carrier 1 to which the catalyst 24 attaches. As a result, the distribution of the density of the catalyst 24 in the carrier 1 can be precisely derived.

Second Embodiment

A second embodiment is a method of manufacturing the carrier 1 according to the first embodiment, and includes a process to place closing members 30 on the first end surface 1a and the second end surface 1b of the carrier 1.

Figure 3:
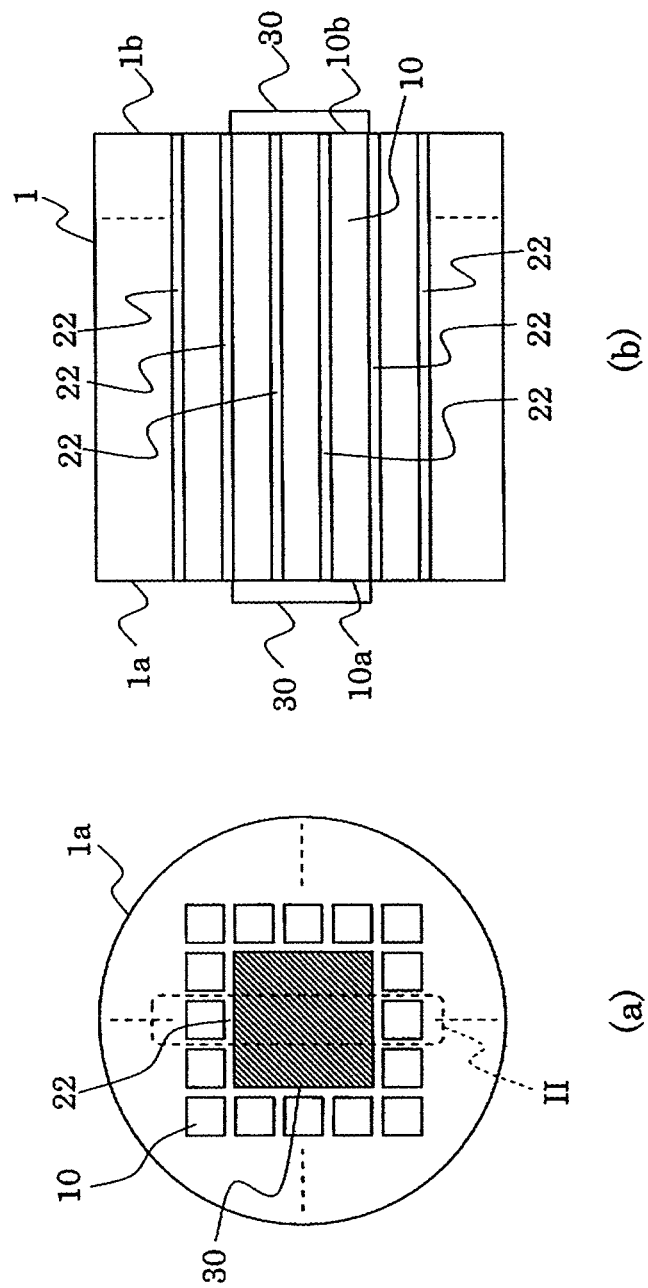
FIG. 3(a) is a front view of the carrier 1 before the attachment of the catalyst 24 according to the second embodiment.
FIG. 3(b) is a cross-sectional view of the part II of the carrier 1.

FIG. 3(a) is a front view of the carrier 1 before the attachment of the catalyst 24 according to the second embodiment, and FIG. 3(b) is a cross-sectional view of the part II of the carrier 1.

The carrier 1 before the attachment of the catalyst 24 includes multiple holes 10. The hole 10 includes a first opening portion 10a and a second opening portion 10b on the opposite side of the first opening portion 10a. The first opening portion 10a opens on the first end surface 1a. The second opening portion 10b opens on the second end surface 1b.

An arrangement of the multiple holes 10 on the first end surface 1a is the same as an arrangement obtained by replacing the attachment holes 12 and the non-attachment holes 14 by the holes 10 in the arrangement shown in FIG. 1(a). A hole 10 to which the catalyst 24 is attached is the attachment hole 12. A hole 10 to which the catalyst 24 is not attached is the non-attachment hole 14.

(Process 2-1) Process of Closing

The first opening portions 10a and the second opening portions 10b of the part (the three-by-three holes 10 at the center, refer to FIGS. 1(a) and 3(a)) of the multiple holes 10 are closed by the closing member 30. Though FIG. 3(a) shows the closing member 30 resting on the first end surface 1a, the closing member 30 is similarly placed on the second end surface 1b.

(Process 2-2) Process of Immersing

Figure 4:
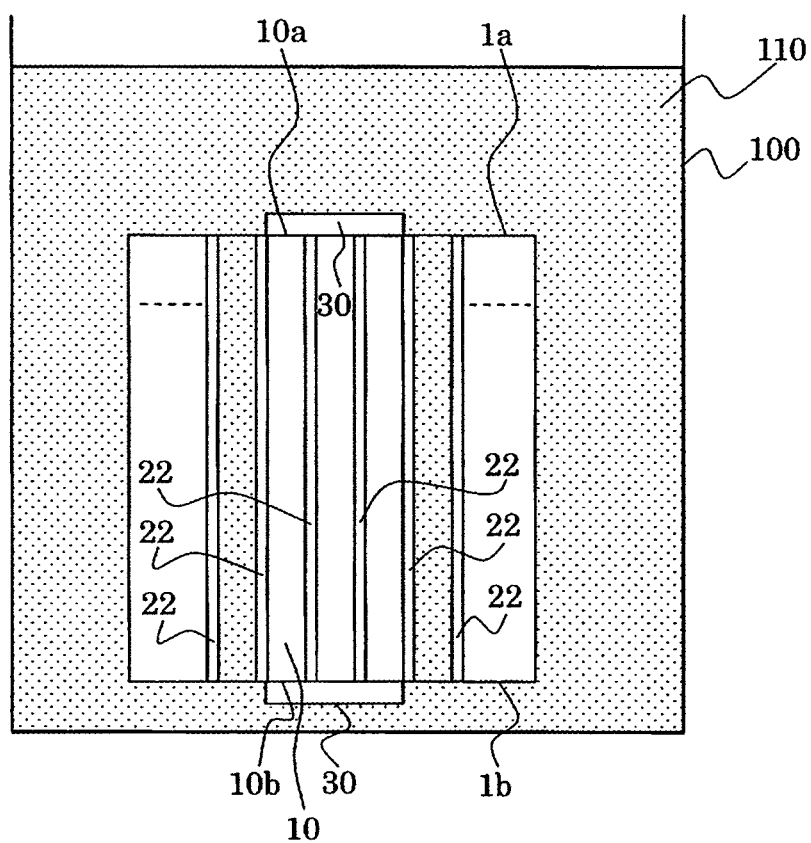
FIG. 4 is a partial cross-sectional view (corresponding to FIG. 3(b)) of the carrier 1 according to the second embodiment.

FIG. 4 is a partial cross-sectional view (corresponding to FIG. 3(b)) of the carrier 1 according to the second embodiment.

A container 100 stores a solution 110 in which a catalyst or promoter is dissolved as a solute. In the solution 110, a catalyst used for automobiles (such as three-way catalyst, oxidation catalyst, and reduction catalyst) or a promoter is dissolved as the solute. Alternatively, in the solution, a catalyst or promoter used as an electrode of a fuel cell is dissolved as a solute. This holds true for the solution 110 according to third to fifth embodiments.

It should be noted that a description will be given of the embodiments of the present invention assuming that the solute of the solution 110 is the catalyst 24.

After the closing members 30 are placed on the first end surface 1a and the second end surface 1b, the carrier 1 is immersed in the solution 110. It should be noted that the liquid surface of the solution 110 is preferably higher than the first end surface 1a and the second end surface 1b.

Then, the solution 110 will not flow into the holes 10 (three holes 10 at the center in FIG. 4), the first opening portion 10a and second opening portion 10b of which are closed by the closing members 30. As a result, these holes 10 become non-attachment holes 14.

On the other hand, the solution 110 flows into the rest of the holes 10 (two holes 10 on both ends in FIG. 4). As a result, the catalyst 24, which is the solute of the solution 110, attaches to (the partition walls 22 enclosing) these holes 10, resulting in the attachment holes 12.

The carrier 1 manufactured in this way becomes the carrier 1 as shown in FIG. 1.

It is conceivable to immerse the carrier 1 in the solution 110 without the closing by the closing members 30 in processes other than the processes 2-1 and 2-2. As a result, it is possible to attach multiple types of catalysts and promoters in the attachment holes 12 and non-attachment holes 14 (the same holds true for the third to fifth embodiments).

For example, it is assumed that the solution 110, in which the catalyst C is used as a solute, is used in the process 2-2. Moreover, it is assumed that solutes of the solution 110 in which the carrier 1 without the closing by the closing members 30 is immersed are the catalyst A and catalyst B. As a result, while catalysts A, B, and C are attached to the attachment holes 12, only the catalysts A and B are attached to the non-attachment holes 14, but the catalyst C is not.

It should be noted that the description has been given of the embodiment of the present invention assuming that the solute of the solution 110 is the catalyst 24. However, in place of the solution 110, a suspension in which the catalyst 24 is distributed may be used. In other words, the solution 110 or the suspension may be used as long as the catalyst (predetermined component) 24 is present therein (the same holds true for the third to fifth embodiments).

Third Embodiment

The third embodiment is a method of manufacturing the carrier 1 according to the first embodiment, and includes a process of placing the closing member 30 on the first end surface 1a of the carrier 1, and a process of spraying a solution.

The carrier 1 before the attachment of the catalyst 24 includes the multiple holes 10. The hole 10 includes the first opening portion 10a and the second opening portion 10b on the opposite side of the first opening portion 10a. The first opening portion 10a opens on the first end surface 1a. The second opening portion 10b opens on the second end surface 1b.

An arrangement of the multiple holes 10 on the first end surface 1a is the same as the arrangement obtained by replacing the attachment holes 12 and the non-attachment holes 14 by the holes 10 in the arrangement shown in FIG. 1(a). A hole 10 to which the catalyst 24 is attached is the attachment hole 12. A hole 10 to which the catalyst 24 is not attached is the non-attachment hole 14.

Figure 5:
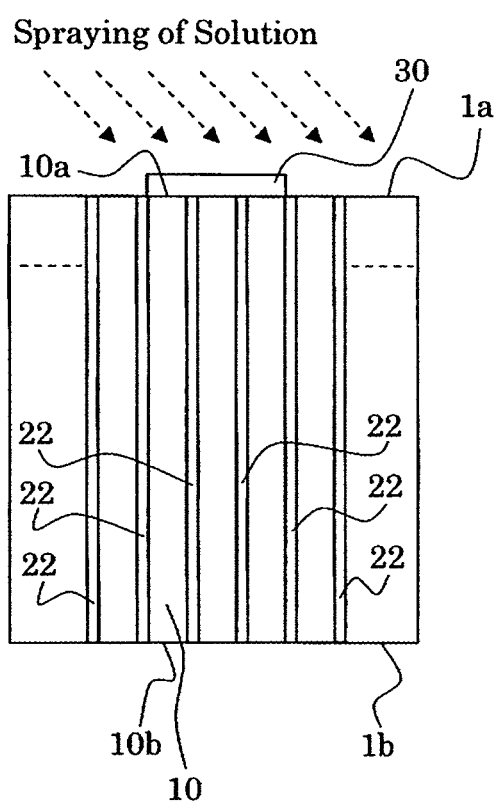
FIG. 5 shows a partial cross-sectional view (corresponding to FIG. 3(b)) of the carrier 1 according to the third embodiment.

FIG. 5 shows a partial cross-sectional view (corresponding to FIG. 3(b)) of the carrier 1 according to the third embodiment.

(Process 3-1) Process of Closing

The first opening portions 10a of the part (the three-by-three holes 10 at the center, refer to FIGS. 1(a) and 3(a)) of the multiple holes 10 are closed by the closing member 30. It should be noted it is not necessary to place the closing member 30 on the second end surface 1b.

(Process 3-2) Process of Spraying

The solution in which a catalyst or promoter is dissolved as a solute is sprayed from above toward the first end surface 1a.

Then, the solution will not flow into the holes 10 (three holes 10 at the center in FIG. 5) the first opening portions 10a of which are closed by the closing member 30. As a result, these holes 10 become non-attachment holes 14.

On the other hand, the solution flows into the rest of the holes 10 (two holes 10 on both ends in FIG. 4.). As a result, the catalyst 24, which is the solute of the solution 110, attaches to (the partition walls 22 enclosing) these holes 10, resulting in the attachment holes 12.

The carrier 1 manufactured in this way becomes the carrier 1 as shown in FIG. 1.

Fourth Embodiment

The fourth embodiment is a method of manufacturing the carrier 1 according to the first embodiment, and includes a process of placing the closing member 30 on the second end surface 1b of the carrier 1, and a process of immersing the carrier 1 in the solution.

The carrier 1 before the attachment of the catalyst 24 includes the multiple holes 10. The hole 10 includes the first opening portion 10a and the second opening portion 10b on the opposite side of the first opening portion 10a. The first opening portion 10a opens on the first end surface 1a. The second opening portion 10b opens on the second end surface 1b.

An arrangement of the multiple holes 10 on the first end surface 1a is the same as the arrangement obtained by replacing the attachment holes 12 and the non-attachment holes 14 by the holes 10 in the arrangement shown in FIG. 1(a). A hole 10 to which the catalyst 24 is attached is the attachment hole 12. A hole 10 to which the catalyst 24 is not attached is the non-attachment hole 14.

(Process 4-1) Process of Closing

The second opening portions 10b of the part (the three-by-three holes 10 at the center, refer to FIGS. 1(a) and 3(a)) of the multiple holes 10 are closed by the closing member 30. It should be noted it is not necessary to place the closing member 30 on the first end surface 1a.

(Process 4-2) Process of Immersing

Figure 6:
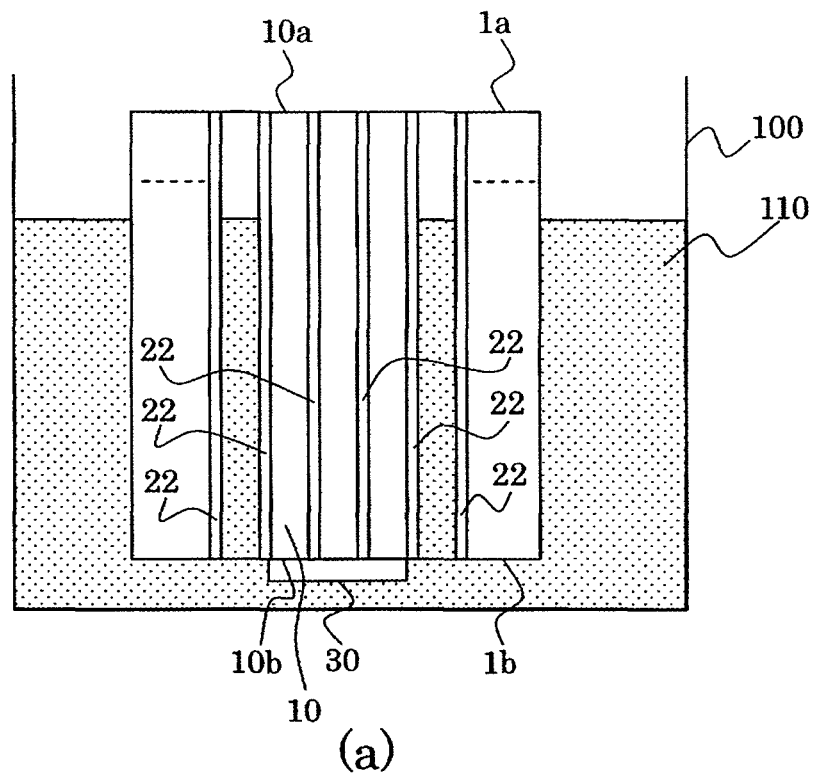
Figure 6:
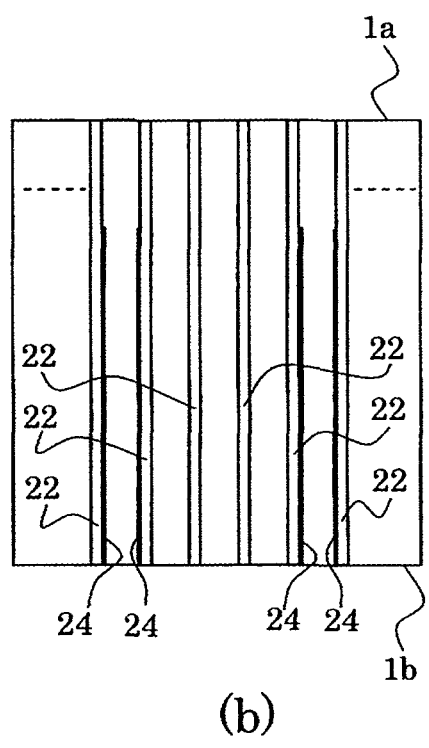

FIGS. 6(a) and 6(b) are partial cross-sectional views of the carrier 1 according to the fourth embodiment, in which FIG. 6(a) is a partial cross-sectional view of the carrier 1 when the carrier 1 is being immersed in the solution 110 (corresponding to FIG. 3(b)), and FIG. 6(b) is a partial cross-sectional view of the carrier 1 after the immersion in the solution 110 (corresponding to FIG. 3(b)).

The container 100 stores the solution 110 in which a catalyst or a promoter is dissolved as a solute. After the closing member 30 is placed on the second end surface 1b, the carrier 1 is immersed in the solution 110. It should be noted that the liquid surface of the solution 110 is configured so as to be higher than the second end surface 1b, and so as to be lower than the first end surface 1a.

Then, the solution 110 will not flow into the holes 10 (three holes 10 at the center in FIG. 6(a)) the second opening portions 10b of which are closed by the closing member 30. As a result, these holes 10 become non-attachment holes 14.

On the other hand, the solution 110 flows into the rest of the holes 10 (two holes 10 on both ends in FIG. 6(a)). As a result, the catalyst 24, which is the solute of the solution 110, attaches to (the partition walls 22 enclosing) these holes 10, resulting in the attachment holes 12. However, the liquid surface of the solution 110 reaches only a mid level of the holes 10, and the catalyst 24 thus reaches only the mid level of the holes 10 (refer to FIG. 6(b)).

The state of the carrier 1 manufactured in this way and viewed from the first end surface 1a is the same as that in FIG. 1(a). It should be noted that the partial cross-sectional view of the carrier 1 manufactured as described above is like FIG. 6(b). The cross section of the non-attachment hole 14 is the same as that shown in FIG. 1(a). However, the cross section of the attachment hole 12 is different from that in FIG. 1(a), and the catalyst 24 has reached only to the mid level of (the partition walls 22 enclosing) the attachment hole 12.

Fifth Embodiment

The fifth embodiment is a method of manufacturing the carrier 1 according to the first embodiment, and the carrier 1 is arranged sideway.

Figure 7:
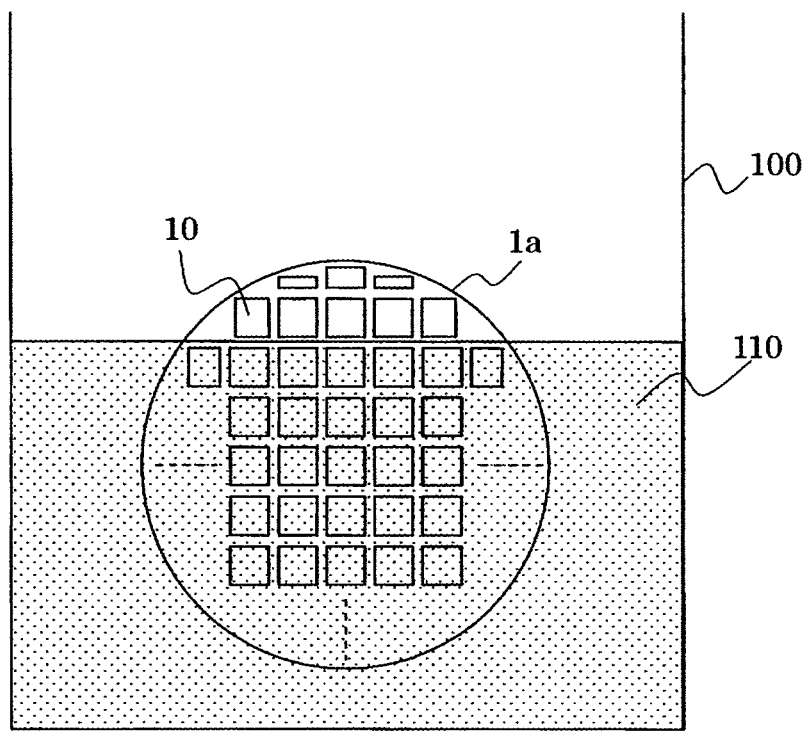
FIG. 7 is a front view when the carrier 1 according to the fifth embodiment is immersed in the solution 110.

FIG. 7 is a front view when the carrier 1 according to the fifth embodiment is immersed in the solution 110.

The carrier 1 before the attachment of the catalyst 24 includes the multiple holes 10. The hole 10 includes the first opening portion 10a and the second opening portion 10b on the opposite side of the first opening portion 10a. The first opening portion 10a opens on the first end surface 1a. The second opening portion 10b opens on the second end surface 1b.

A hole 10 to which the catalyst 24 is attached is the attachment hole 12. A hole 10 to which the catalyst 24 is not attached is the non-attachment hole 14.

(Process 5-1) Process of Immersing

The container 100 stores the solution 110 in which a catalyst or a promoter is dissolved as a solute. The carrier 1 is immersed in the solution 100 so that the liquid surface of the solution 110 is lower than the first opening portions 10a of a part of the multiple holes 10. In order to achieve this state, it is conceived that the carrier 1 is turned sideway, and is immersed in the solution 110, for example.

Then, the solution 110 will not flow into the holes 10 above the liquid surface of the solution 110. As a result, these holes 10 become non-attachment holes 14.

On the other hand, the solution 110 flows into the holes 10 below the liquid surface of the solution 110. As a result, the catalyst 24, which is the solute of the solution 110, attaches to (the partition walls 22 enclosing) these holes 10, resulting in the attachment holes 12.

The invention claimed is:

1. An attachment quantity measurement device comprising:
   an electromagnetic wave output device that outputs an electromagnetic wave to be measured having a frequency equal to or higher than 0.01 THz and equal to or lower than 100 THz toward a carrier, including an attachment hole to which a catalyst is attached and a non-attachment hole to which the catalyst is not attached;
   an electromagnetic wave detector that detects the electromagnetic wave to be measured which has transmitted through the carrier;
   a reference value obtainer configured to obtain a reference value, based on the electromagnetic wave detected by the electromagnetic wave detector, the reference value being one of an absorption rate, a group delay, and a dispersion of the electromagnetic wave to be measured in the non-attachment hole; and an attachment quantity obtainer configured to obtain, based on the electromagnetic wave detected by the electromagnetic wave detector and the reference value obtained by the reference value obtainer, at least one of a weight and a density of the catalyst present in the attachment hole.

2. The attachment quantity measurement device according to claim 1, wherein the direction of an extension of the attachment hole and the direction of an extension of the non-attachment hole are parallel with each other.

3. The attachment quantity measurement device according to claim 1, wherein the carrier comprises two end surfaces that are parallel with each other, and wherein the attachment hole and the non-attachment hole are open on each of the two end surfaces.

4. The attachment quantity measurement device according to claim 1, further comprising:
a rotational driver that rotates one of the carrier and a travel direction of the electromagnetic wave to be measured about a rotational axis, the rotational axis being a line in a direction perpendicular to the travel direction of the electromagnetic wave to be measured; and
a linear driver that moves one of the carrier and the travel direction of the electromagnetic wave to be measured in a direction perpendicular to the travel direction of the electromagnetic wave to be measured and the rotational axis,
wherein the electromagnetic wave detector detects the electromagnetic wave to be measured while the rotational driver and the linear driver are operating.

5. The attachment quantity measurement device according to claim 1, wherein gas flows from one end of the attachment hole, substantially passes through the attachment hole, and is output from an other end of the attachment hole,
gas flows from one end of the non-attachment hole, substantially passes through the non-attachment hole, and is output from an other end of the non-attachment hole.

6. The attachment quantity measurement device according to claim 1,
wherein the attachment quantity obtainer obtains the at least one of the weight and the density of the catalyst present in the attachment hole of the carrier, based on the reference value obtained from the non-attachment hole of the same carrier by the reference value obtainer.

7. The attachment quantity measurement device according to claim 1, wherein the reference value obtainer obtains the reference value, before exhaust gas passes through the carrier, and the attachment quantity obtainer obtains the at least one of the weight and the density of the catalyst before exhaust gas passes through the carrier.

8. The attachment quantity measurement device according to claim 1, wherein the reference value obtainer obtains the absorption rate $\alpha 0$ of the electromagnetic wave transmitted through the non-attachment hole of the carrier,
the attachment quantity obtainer comprises a memory that stores an increase rate $\beta$ of the absorption rate of the electromagnetic wave with respect to the density of the catalyst, the increase rate $\beta$ being stored the memory before the electromagnets wave detector detects the electromagnetic wave transmitted through the carrier,
the attachment quantity obtainer obtains an absorption rate $\alpha$ of the electromagnetic wave transmitted through the attachment hole of the carrier, and
the attachment quantity obtainer obtains the density of the catalyst by calculating $(\alpha-\alpha 0)/\beta$.

9. An attachment quantity measurement method using an attachment quantity measurement device, including an electromagnetic wave output device that outputs an electromagnetic wave to be measured having a frequency equal to or higher than 0.01 THz and equal to or lower than 100 THz toward a carrier, including an attachment hole to which a catalyst is attached and a non-attachment hole to which the catalyst is not attached, the attachment quantity measurement method comprising:
detecting the electromagnetic wave to be measured which has transmitted through the carrier,
obtaining a reference value, based on the detected electromagnetic wave to be measured, the reference value being one of an absorption rate, a group delay, and a dispersion of the electromagnetic wave to be measured in the non-attachment hole; and
obtaining, based on the detected electromagnetic wave to be measured and the obtained reference value, at least one of a weight and a density of the catalyst present in the attachment hole.

10. The attachment quantity measurement method according to claim 9, wherein the direction of an extension of the attachment hole and the direction of an extension of the non-attachment hole are parallel with each other.

11. The attachment quantity measurement method according to claim 9, wherein the carrier comprises two end surfaces that are parallel with each other, and wherein the attachment hole and the non-attachment hole are open on each of the two end surfaces.

12. The attachment quantity measurement method according to claim 9, further comprising:
rotating one of the carrier and a travel direction of the electromagnetic wave to be measured about a rotational axis, the rotational axis being a line in a direction perpendicular to the travel direction of the electromagnetic wave to be measured; and
moving one of the carrier and the travel direction of the electromagnetic wave to be measured in a direction perpendicular to the travel direction of the electromagnetic wave to be measured and the rotational axis,
wherein the electromagnetic wave to be measured is detected while the rotating and the moving are performed.

13. The attachment quantity measurement method according to claim 9, wherein gas flows from one end of the attachment hole, substantially passes through the attachment hole, and is output from an other end of the attachment hole,
gas flows from one end of the non-attachment hole, substantially passes through the non-attachment hole, and is output from an other end of the non-attachment hole.

14. A non-transitory computer-readable medium having a program of instructions for execution by a computer to perform an attachment quantity measurement process using an attachment quantity measurement device, including an electromagnetic wave output device that outputs an electromagnetic wave to be measured having a frequency equal to or higher than 0.01 THz and equal to or lower than 100 THz toward a carrier, including an attachment hole to which a catalyst is attached and a non-attachment hole to which the catalyst is not attached; and an electromagnetic wave detector that detects the electromagnetic wave to be measured which has transmitted through the carrier, the attachment quantity measurement process comprising:
obtaining a reference value, based on the electromagnetic wave detected by the electromagnetic wave detector, the reference value being one of an absorption rate, a group delay, and a dispersion of the electromagnetic wave to be measured in the non-attachment hole; and obtaining, based on the electromagnetic wave detected by the electromagnetic wave detector and the obtained reference value, at least one of a weight and a density of the catalyst present in the attachment hole.

15. The non-transitory computer-readable medium according to claim 14, wherein the direction of an extension of the attachment hole and the direction of an extension of the non-attachment hole are parallel with each other.

16. The non-transitory computer-readable medium according to claim 14, wherein the carrier comprises two end surfaces that are parallel with each other, and wherein the attachment hole and the non-attachment hole are open on each of the two end surfaces.

17. The non-transitory computer-readable medium according to claim 14, wherein the attachment quantity measurement process further comprises:
rotating one of the carrier and a travel direction of the electromagnetic wave to be measured about a rotational axis, the rotational axis being a line in a direction perpendicular to the travel direction of the electromagnetic wave to be measured; and
moving one of the carrier and the travel direction of the electromagnetic wave to be measured in a direction perpendicular to the travel direction of the electromagnetic wave to be measured and the rotational axis,
wherein the electromagnetic wave to be measured is detected while the rotating and the moving are performed.

18. The non-transitory computer-readable medium according to claim 14, wherein gas flows from one end of the attachment hole, substantially passes through the attachment hole, and is output from an other end of the attachment hole,
gas flows from one end of the non-attachment hole, substantially passes through the non-attachment hole, and is output from an other end of the non-attachment hole.

* * * * *